United States Patent [19]

Edwards

[11] Patent Number: 5,160,499
[45] Date of Patent: Nov. 3, 1992

[54] PURIFICATION OF 1,1,1,2-TETRAFLUOROETHANE

[75] Inventor: Derek W. Edwards, Runcorn, England

[73] Assignee: Imperial Chemical Industries PLC, London, England

[21] Appl. No.: 849,350

[22] Filed: Mar. 11, 1992

[30] Foreign Application Priority Data

Mar. 14, 1991 [GB] United Kingdom ............... 9105421

[51] Int. Cl.$^5$ ............................................. C07C 17/38
[52] U.S. Cl. .................................................. 570/179
[58] Field of Search ........................................ 570/179

[56] References Cited

U.S. PATENT DOCUMENTS

| | | | |
|---|---|---|---|
| 4,906,796 | 3/1990 | Yates | 570/179 |
| 4,940,824 | 7/1990 | Yates | 570/179 |
| 4,950,816 | 8/1990 | Tung | 570/179 |

*Primary Examiner*—Alan Siegel
*Attorney, Agent, or Firm*—Cushman, Darby & Cushman

[57] ABSTRACT

A process for the removal of 1-chloro-2,2-difluoroethylene from 1,1,1,2-tetrafluoroethane which process comprises contacting 1,1,1,2-tetrafluoroethane containing 1-chloro-2,2-difluoroethylene with a zeolite containing strontium cations.

The zeolite containing strontium cations may be produced by ion-exchange with a commercially available zeolite, for example an A-type zeolite or a chabazite.

11 Claims, 2 Drawing Sheets

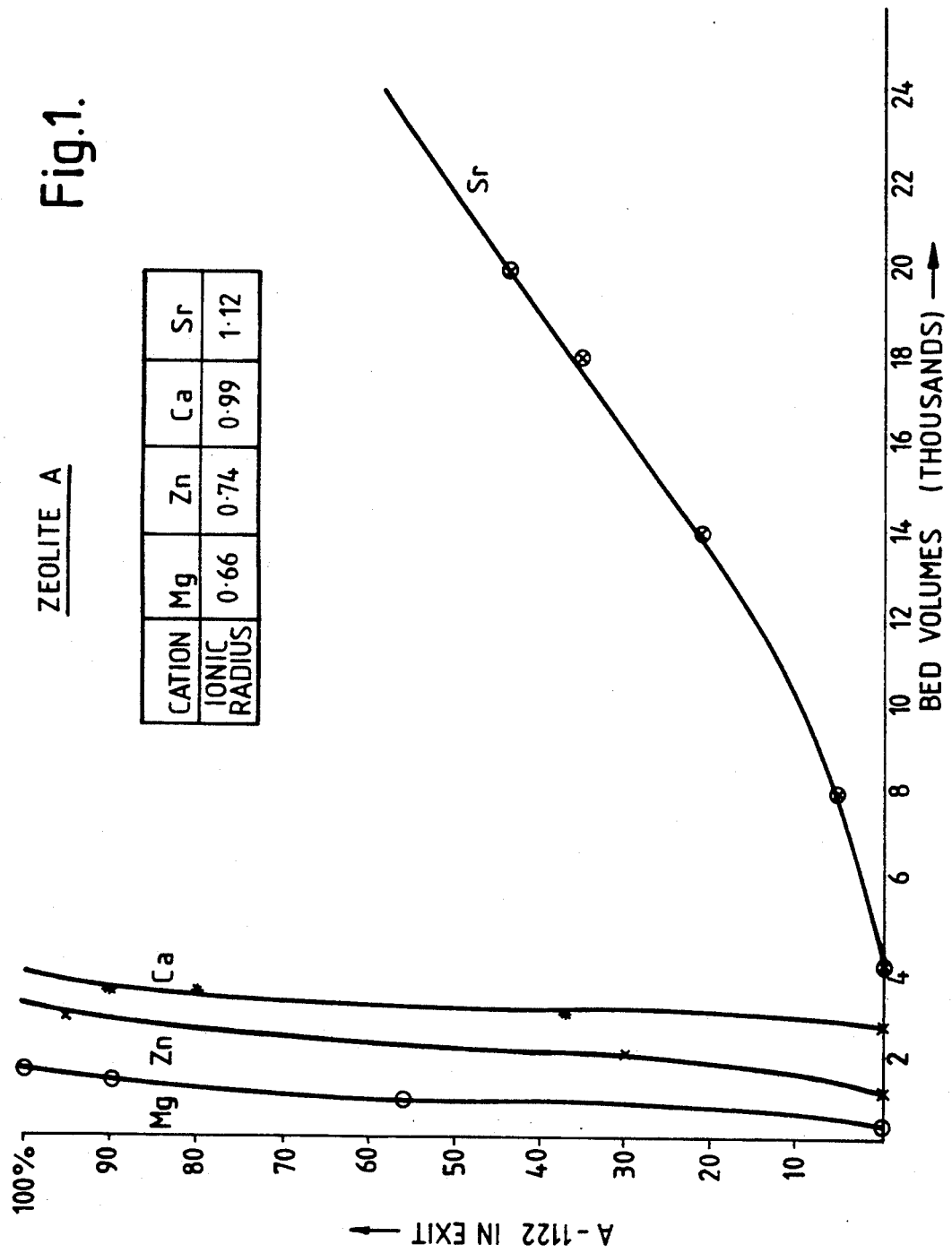

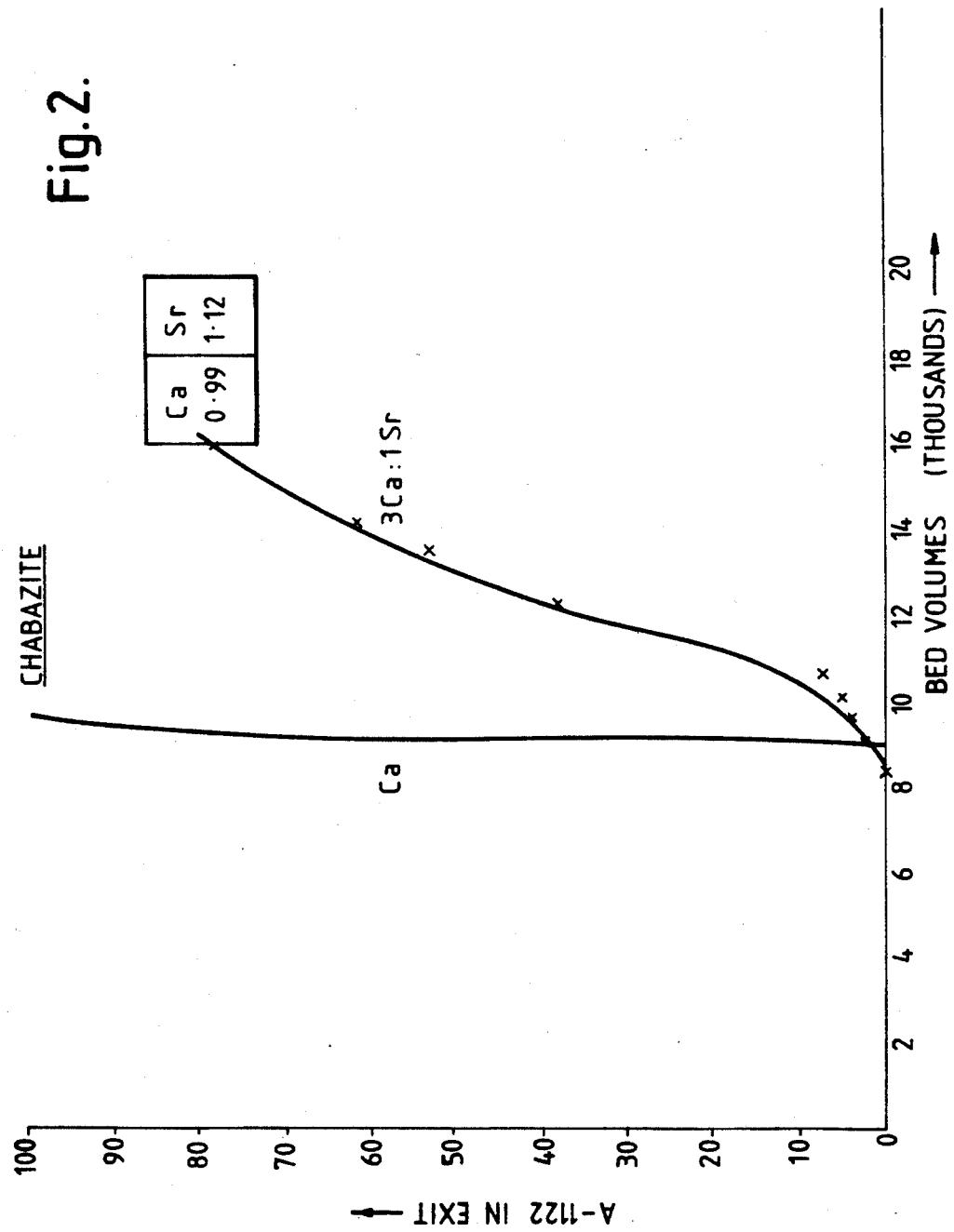

PURIFICATION OF 1,1,1,2-TETRAFLUOROETHANE

This invention relates to a process for the purification of 1,1,1,2-tetrafluoroethane and in particular to a process for the removal of 1-chloro-2,2-difluoroethylene from 1,1,1,2-tetrafluoroethane.

In recent years chlorofluorocarbons (CFCs), which are used on a large scale around the world, have been perceived as having an adverse effect on the ozone layer and/or as contributing to global warming. CFCs are used, for example, as refrigerants, as foam blowing agents, as cleaning solvents and as propellants for aerosol sprays in which the variety of applications is virtually unlimited. Consequently, attempts have been made to find suitable replacements which will perform satisfactorily in the many applications in which CFCs are used but which will not have the aforementioned damaging effects. The search for suitable replacements has in general centered on fluorocarbons which do not contain chlorine. The hydrofluorocarbon, 1,1,1,2-tetrafluoroethane, also known as HFA 134a, has been of particular interest as one such replacement, in particular as a replacement for dichlorodifluoromethane (CFC 12) in refrigeration applications, but also for use in other applications.

HFA 134a may be produced in a variety of ways, amongst which may be mentioned fluorination of a CFC or HCFC, for example 1-chloro-2,2,2-trifluoroethane (HCFC 133a) with hydrogen fluoride or an alkali metal fluoride; a catalyst such as chromia, halogenated chromia or chromium oxyhalide may be employed to facilitate the reaction with hydrogen fluoride in the gas phase.

However, a characteristic of known processes for the production of HFA 134a is that many by-products tend to be produced. Some of the by-products are easy to separate by distillation whilst others are relatively harmless since they are not toxic and their presence does not greatly alter the physical properties of the 134a. However a by-product which is toxic and which thus must be removed or at least reduced in concentration to extremely low levels, for example below 10 ppm, is 1-chloro-2,2-difluoroethylene (HCFC 1122). HCFC-1122 has a boiling point close to that of HFA 134a, and it is thus difficult to separate HCFC 1122 and HFA 134a by distillation.

Processes for the removal of HCFC 1122 from HFA 134a have been described previously. Thus, for example, in U.S. Pat. No. 4,129,603 there is described a process for removing HCFC 1122 from HFA 134a comprising contacting impure HFA 134a with an aqueous solution of a metal permanganate and in U.S. Pat. No. 4,158,675 there is described a process comprising contacting impure HFA 134a with hydrogen fluoride in the presence of a chromium catalyst at 100° C. to 275° C.

It has been proposed to use certain types of molecular sieve for the removal of HCFC 1122 from HFA 134a. Thus, in U.S. Pat. No. 4,906,790 there is disclosed a process for the removal of HCFC 1122 from HFA 134a in which an HFA 134a stream is passed over a molecular sieve which has a pore size of 3.8 to 4.8 Angstroms; the sieve may be carbon, zeolite 5A or calcium chabazite. However, the use of the zeolites disclosed in the aforementioned U.S. Patent suffers from the disadvantage that the selectivity of the zeolite, that is the amount of HCFC 1122 which is adsorbed by the zeolite as a proportion of the HFA 134a and other hydrofluorocarbon by-products adsorbed by the zeolite, may be barely satisfactory for practical adoption of the process.

The present invention is intended to remedy this disadvantage and resides in the removal of 1-chloro-2,2-difluoroethylene (HCFC 1122) from 1,1,1,2-tetrafluoroethane (HFA 134a) utilising a zeolite which removes HCFC 1122 from a mixture of HFA 134a, HCFC 1122 and optionally other hydrofluorocarbon by-products with a greater degree of selectivity than the zeolites proposed hitherto.

According to the present invention there is provided a process for the removal of 1-chloro-2,2-difluoroethylene (HCFC 1122) from 1,1,1,2-tetrafluoroethane (HFA 134a) which process comprises contacting HFA 134a containing HCFC 1122 with a zeolite containing strontium cations.

The presence of strontium cations ($Sr^{++}$) in the structure of the zeolite leads to a substantial improvement in the selectivity of the zeolite for adsorbing HCFC 1122, i.e. the proportion of HCFC 1122 relative to other HFC's and HCFC's that is adsorbed per unit volume of the zeolite may be increased.

It is believed that this improvement in selectivity may be brought about by the influence of cation size on the effective size and shape of the pores within the zeolite structure.

The mean pore size of the zeolite containing strontium cations may be in the range from about 3.5 Å to about 4.8 Å. Preferably however, the mean pore size of the zeolite containing strontium cations is from about 3.5 Å to about 4.5 Å and more preferably from about 3.6 Å to about 4.2 Å.

Changes in electronic interactions and changes in the shape and configuration of the adsorption sites within the zeolite structure are believed also to influence the improved performance of zeolites containing strontium cations.

The preferred zeolites of the present invention are strontium ion-exchanged forms of common zeolites, the strontium ion-exchanged form having a mean pore size in the range from about 3.5 Å to about 4.8 Å, that is they are zeolites which have been produced by strontium ion-exchange with commercially available starting zeolites. The starting zeolite may be, for example, an "A"-type zeolite such as zeolite 4A or zeolite 5A. Alternatively, the starting zeolite may be a chabazite, for example calcium chabazite, commercially available as AW-500.

The process of ion exchange to produce the ion-exchanged form of zeolite is a conventional technique, described for example in The Journal of Physical Chemistry, 66, 812–16 (1962). Typically, the starting zeolite, for example zeolite 5A may be immersed in a concentrated aqueous solution of a strontium salt. The anion of the strontium salt is generally irrelevant for the purposes of the present invention but is preferably a halide, and particularly a chloride, for example, $SrCl_2.6H_2O$ since strontium halides are water soluble. The solution containing the zeolite may be stirred for the appropriate period of time, for example from a few hours, say 2-3 hours, to a few days, say 2-3 days, at room or elevated temperature, then the liquid decanted and the solid zeolite washed with water and dried.

The degree of ion-exchange, that is the % of the original cation in the starting zeolite which is replaced by strontium, for example, the % of $Na^+$ ions replaced in starting zeolite A, may be controlled by, inter alia, varying the time for which the starting zeolite is immersed in the strontium salt solution. The degree of ion-exchange may be varied within a wide range depending upon, inter alia, the starting zeolite, it being generally observed that as the degree of exchange increases, so the selectivity of the ion-exchanged form of zeolite for removal of HCFC 1122 increases. Where the starting zeolite is zeolite A, it is preferred for optimum results that the degree of ion-exchange is at least 30%, more preferably at least 50% whilst where the starting zeolite is calcium chabazite, the degree of exchange is preferably at least 10% and more preferably at least 25%. However, the degree of ion-exchange may be significantly less than the above ranges.

Overall, the degree of ion-exchange will typically be at least 10%, preferably at least 25% and especially at least 50%.

Prior to use of the strontium-exchanged zeolite in the process of the invention, the zeolite should be dried and this may be achieved, for example, by heating the zeolite to a temperature of between about 200° C. and about 400° C. in a nitrogen atmosphere at atmospheric pressure or at a lower temperature under sub-atmospheric pressure.

In the process of the invention, HFA 134a may be contacted with the zeolite containing strontium cations by passing a stream of HFA 134a in the liquid or vapour phase over a bed of zeolite particles. The bed may be a fixed bed. Alternatively various other techniques, known in the art, may be used for contacting an HFA 134a stream with the zeolite, such as for example, contacting the stream with a fluidised or moving bed of zeolite particles. Selection of the particle size and bed shape may be varied within a broad range and may be determined according to known principles. The zeolite particle size depends at least to some extent upon whether vapour phase or liquid phase contacting is employed and upon the scale of the process, but overall the particle size will be in the range from about 1 micrometer to about 5 centimeters, preferably from about 50 micrometers to about 10 millimeters.

The hourly space velocity of the HFA 134a stream over the zeolite may be varied within a wide range. Generally, HFA 134a vapour may be passed over the zeolite with a gas hourly space velocity in the range from about 130 to about 3600 hr$^{-1}$, although the gas hourly space velocity may be much greater than this, particularly at lower temperatures. The corresponding liquid hourly space velocity for liquid phase operation is 1 to 30 hr$^{-1}$.

The temperature at which the purification process is carried out will typically be in the range from about −10° to about 100° C. The pressure at which the process is carried out may be dependent to some extent upon whether liquid or vapour phase contacting is desired but may be between 0.1 and 9 bar.

Typically, the HFA 134a as produced by conventional processes contains between 10 and 10,000 ppm HCFC 1122 although it may contain a substantially higher concentration of HCFC 1122. Use of strontium-exchanged zeolites allows the removal of HCFC 1122 from HFA 134a to a very low level, generally below 5 ppm, and even below 2 ppm.

HFA 134a as produced by known processes may contain further contaminants in addition to HCFC 1122. These contaminants include, for example, single-carbon and two-carbon species containing hydrogen, chlorine and fluorine, as well as unreacted hydrogen fluoride and by-product hydrogen chloride (which is a major by-product from most known HFA 134a production processes). The hydrogen fluoride and hydrogen chloride can be removed by known techniques; preferably, since hydrogen fluoride and hydrogen chloride may attack the zeolites used in the process of the invention, the removal of hydrogen fluoride and hydrogen chloride is carried out prior to contacting the HFA 134a stream with the zeolite. Other contaminants are commonly present in only very small amounts and many may be removed by distillation. The zeolites of the present invention have little capacity for adsorption of these minor contaminants and adsorption of HCFC 1122 is therefore highly selective with respect to these contaminants.

The adsorbent zeolite bed will require regeneration or reactivation when its capacity for adsorbing HCFC 1122 has been filled. Regeneration may be by heating the bed with a gas stream, usually nitrogen or air, to desorb the HCFC 1122. However, the frequency with which the bed must be regenerated may be significantly reduced when compared with a bed of the zeolites used heretofore. After the bed has been heated and HCFC 1122 fully removed or even partially removed from it, it may be cooled and re-introduced into service. The conditions required for optimal regeneration of the adsorbent will be determined by the adsorbent used and the available utilities and are readily determined by simple routine experiment. Typically, heating the bed of adsorbent to between about 150° C. and about 400° C. within a stream of nitrogen gas or air provides satisfactory regeneration.

The invention is illustrated by the following examples.

EXAMPLE 1

ION EXCHANGED FORMS OF ZEOLITE A (a) Preparation of ion-exchanged forms of zeolite A The procedure described below was carried out to prepare three samples of ion-exchanged forms of zeolite A. In each of the three cases, the procedure was the same except that the metal salt used in the form of an aqueous solution was respectively as follows:

|   | MOLALITY |
|---|---|
| (a) MgCl$_2$.6H$_2$O | 0.00260 |
| (b) ZnCl$_2$ | 0.00156 |
| (c) SrCl$_2$.6H$_2$O | 0.000857 |

200 g of the sodium form of zeolite A (supplied by BDH) having an average particle size of 2 microns was immersed in a concentrated aqueous metal salt solution and the mixture was stirred at room temperature for 3 days. At the end of this time the zeolite was allowed to settle and the solution was decanted. The solid zeolite was then washed with de-ionised water, air dried for 24 hours at room temperature and then vacuum dried at 80° C. until there was no further measurable loss of weight. The ion-exchanged form of zeolite A was then pressed and sieved until particles of average size 1 millimeter were obtained.

The strontium cation-exchanged zeolite was then analysed to determine its sodium and strontium content, and hence the degree of ion-exchange. Sodium and strontium were determined as present in the zeolite in the molar ratio Sr 1.7:Na 1.0. Each strontium inserted into the zeolite replaces two sodium ions due to strontium ions having twice the valency of sodium ions and therefore the proportion of sodium which had been replaced was 3.4/4.4 or 77%.

(b) REMOVAL OF HCFC 1122 FROM HFA 134a.

The procedure described below was carried out with each of the three samples described above and additionally with commercially available Zeolite 5A (supplied by BDH and containing calcium cations).

1 g of the cation-exchanged form of zeolite A sample with average particle size of 1 millimeter was packed into a ¼" stainless steel tube and the tube was heated in a stream of nitrogen at 250° C. The tube was then left to cool to 40° C. and a stream of HFA 134a doped with 80 ppm HCFC 1122 was passed through the tube at a flow rate of 10–20 ml/min. The concentration of HCFC 1122 in the exit gas was determined by gas chromatography and the results are shown in graphic form in FIG. 1, in which "bed volumes" is the volume of 134a passed over the zeolite bed divided by the volume of the zeolite bed. The total adsorption and 1122 adsorption of the zeolites are shown in Table 1 below.

TABLE 1

| ZEOLITE | 1122 Adsorption mg/g | Total Adsorption. mg/g |
| --- | --- | --- |
| Mg | 0.5–1.0 | 238 |
| Zn | 0.5–1.0 | 214 |
| Ca | 2.5 | 114 |
| Sr | 4.0–8.0 | 90 |

The results show that the selectivity of the strontium-exchanged zeolite for adsorbing HCFC 1122 present in the stream of HFA 134a is substantially greater than the selectivity of the magnesium of zinc exchanged forms or the calcium form.

EXAMPLE 2

ION-EXCHANGED FORMS OF CALCIUM CHABAZITE (a) Preparation of ion-exchanged forms of Chabazite The procedure described in example 1 (a) was followed to produce a single sample of calcium chabazite exchanged with strontium, except that 200 g of calcium chabazite (AW-500) were immersed in the aqueous metal salt solution, and the metal salt solution used was:

| | MOLALITY |
| --- | --- |
| (a) $SrCl_2.6H_2O$ | 0.000857 |

Inorganic analysis of the ion-exchanged zeolite showed that the degree of ion-exchange was 25%.

(b) REMOVAL OF HCFC 1122 FROM HFA 134a

The procedure described in Example 1 (b) was followed using 1 g of the sample obtained as described above and for comparison, 1 g of calcium chabazite (AW-500). The results are shown in graphic form in FIG. 2.

I claim:

1. A process for the removal of 1-chloro-2,2-difluoroethylene from 1,1,1,2-tetrafluoroethane which process comprises contacting 1,1,1,2-tetrafluoroethane containing 1-chloro-2,2-difluoroethylene with a zeolite containing strontium cations.

2. A process as claimed in claim 1 in which the zeolite has a mean pore size in the range from about 3.5 Å to about 4.8 Å.

3. A process as claimed in claim 1 in which the zeolite has a mean pore size in the range from about 3.6 Å to about 4.5 Å.

4. A process as claimed in any one of claims 1 to 4 in which the zeolite is produced by strontium cation-exchange with a starting zeolite selected from the group consisting of A-type zeolites or a chabazite.

5. A process as claimed in claim 4 in which the starting zeolite is zeolite 5A.

6. A process as claimed in claim 5 in which the degree of cation-exchange is at least 10%.

7. A process as claimed in claim 6 in which the degree of cation-exchange is at least 25%.

8. A process as claimed in claims 1 in which the 1,1,1,2-tetrafluoroethane containing 1-chloro-2,2-difluoroethylene in the liquid or vapour phase is passed over a bed of zeolite particles.

9. A process as claimed in any one of claim 1 in which the temperature is in the range from about 10° C. to about 100° C.

10. A process as claimed in claim 8 in which the 1,1,1,2-tetrafluoroethane containing 1-chloro-2,2-difluoroethylene in the vapour phase is passed over a bed of zeolite particles with a gas hourly space velocity in the range from about 130 to about 3600 $hr^{-1}$.

11. A process as claimed in any one of claim 1 wherein the 1,1,1,2-tetrafluoroethane to be contacted with the zeolite contains from about 10 to about 10,000 ppm of 1-chloro-2,2-difluoroethylene and whereby a product 1,1,1,2-tetrafluoroethane containing less than 5 ppm of 1-chloro-2,2-difluoroethylene is recovered.

* * * * *